United States Patent [19]

Hoffman

[11] 4,224,567
[45] Sep. 23, 1980

[54] APPARATUS FOR MEASURING RESISTANCE CHANGE ONLY IN A CELL ANALYZER AND METHOD FOR CALIBRATING IT

[75] Inventor: Robert A. Hoffman, Los Alamos, N. Mex.

[73] Assignee: The United States of America as represented by the United States Department of Energy, Washington, D.C.

[21] Appl. No.: 957,632

[22] Filed: Nov. 3, 1978

[51] Int. Cl.² .............................................. G01N 27/00
[52] U.S. Cl. .................... 324/71 CP; 324/64
[58] Field of Search ............... 73/432 PS; 364/555; 324/71 CP, 306, 442, 64, 71 R, 439

[56] References Cited

U.S. PATENT DOCUMENTS

| | | | |
|---|---|---|---|
| 2,871,445 | 1/1959 | Carter | 324/30 |
| 3,648,158 | 3/1972 | Parker | 324/30 B |
| 3,764,901 | 10/1973 | Kachel | 324/71 CP |
| 3,791,517 | 2/1974 | Friedman | 324/71 CP |
| 3,793,587 | 2/1974 | Thom | 324/71 CP |
| 3,824,402 | 7/1974 | Mullaney | 250/565 |
| 3,924,180 | 12/1975 | Salzman | 324/71 CP |

FOREIGN PATENT DOCUMENTS 274474  6/1970  U.S.S.R. .

*Primary Examiner*—Michael J. Tokar
*Attorney, Agent, or Firm*—R. V. Lupo; Paul D. Gaetjens; Robert W. Weig

[57] ABSTRACT

The disclosure relates to resistance only monitoring and calibration in an electrical cell analyzer. Sample and sheath fluid flows of different salinities are utilized, the sample flow being diameter modulated to produce a selected pattern which is compared to the resistance measured across the flows.

9 Claims, 1 Drawing Figure

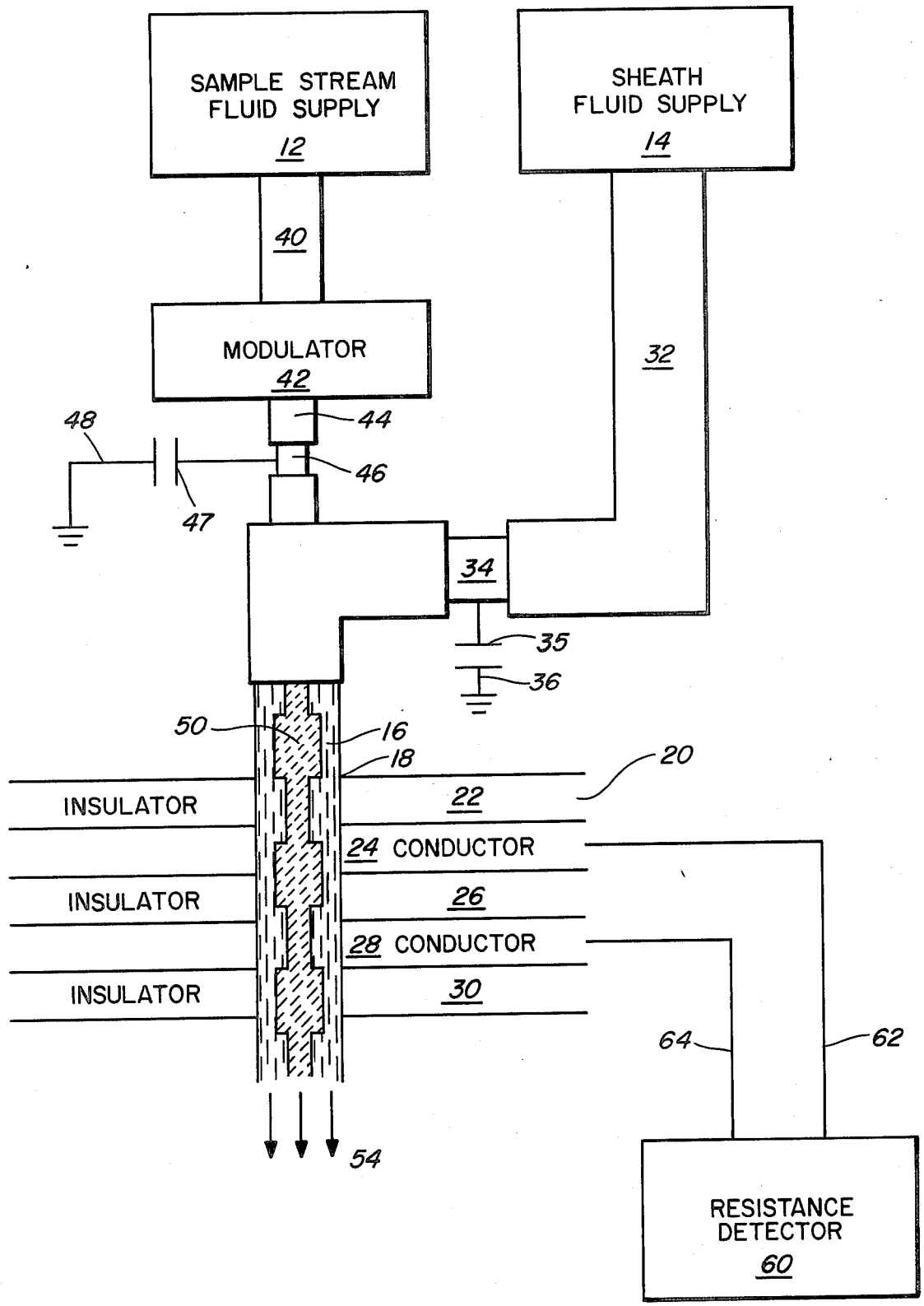
Fig.

APPARATUS FOR MEASURING RESISTANCE CHANGE ONLY IN A CELL ANALYZER AND METHOD FOR CALIBRATING IT

FIELD OF THE INVENTION

The invention relates to cell analyzers and more particularly an apparatus and method for utilizing resistance change only across the orifice in such an analyzer.

BACKGROUND OF THE INVENTION

In cytology, there is an ever-increasing demand for automatic cellular counting, volumetric differentiation and analysis. At the present time, screening of cytological material such as for the detection of cancerous or malignant cells, and for sizing and counting the cells present in a particular amount of material, is typically manually accomplished by a two level screening process. The cells are first prescreened visually by an observer capable of determining which samples apparently contain abnormal cells and to determine the size cell one hopes to count within a sample. The abnormal cell-containing samples are then examined by a trained cytotechnologist or pathologist who makes a final determination as to whether the cells of these samples are indeed cancerous. This method fairly accurately finds cancerous cells but it has a number of disadvantages. First, it is slow, requiring considerable technician time. Second, it is costly due to the human time involved. Third, it is nonquantitative in that the criteria of abnormality as well as the amount of cells present in a particular volumetric sample are primarily subjective. Because of the time and costs involved, it is generally not practicable to examine large populations of individuals using these prior art techniques.

In addition, most of the cellular specimens examined by a medical laboratory are normal. Therefore, the level of alertness and interest of those who do the screening is difficult to maintain. For example, in cytological examination for uterine cervical carcinoma, 98% of the women examined do not have cancer. Thus, personnel turnover may tend to be high and the test results become less quantitative and more costly.

Recently systems have been developed for automatically determining the volumetric distribution of a sample of cells. The output can be used, for example, to normalize light signals from a cell analyzer such as that disclosed in the U.S. Pat. No. 3,824,402 to Mullaney et. al. issued July 16, 1974.

A typical electrical analysis device utilizes orifices having electrodes at either end disposed in the surrounding solution or, disposed within the orifice itself as in U.S. Pat. No. 3,924,180 issued Dec. 2, 1975 to Salzman et al. In either case, the system must be calibrated from time to time.

SUMMARY OF THE INVENTION

In accordance with the present invention, there is provided an apparatus and method for calibrating an electrical cell analyzer comprising a sample stream fluid supply and a sheath stream fluid supply. The sample stream is modulated in accordance with a predetermined pattern and has either a higher or a lower conductivity than the sheath fluid. Electrical measurements are taken of the resistance only change across the fluid stream as it passes through the orifice.

One object of the present invention is to provide calibration for electrical cell analyzers.

The second object of the present invention is to eliminate noise from flow sample and sheath fluid streams.

One advantage of the present invention is that in accordance therewith, resistance change only can be calibrated in electrical cell analyzers.

Another advantage of the present invention is that the structure thereof is inexpensive to make and use.

BRIEF DESCRIPTION OF THE DRAWING

Other objects and advantages of the present invention will be apparent to those skilled in the art from the following description with reference to the appended drawing wherein like numbers denote like parts and wherein:

The FIGURE illustrates a preferred embodiment of the invention.

DETAILED DESCRIPTION OF THE PREFERRED EMBODIMENT OF THE INVENTION

Reference is now made to the FIGURE which shows schematically a sample stream fluid supply 12 and a sheath fluid supply 14. Sheath fluid supply 14 supplies a sheath fluid 16 which passes through an orifice 18 within, for example, a multilayered or laminated body 20 comprising an insulating layer 22, a conductive layer 24, a second insulating layer 26, a second conductive layer 28, and a third insulating layer 30. The structure of the orifice may vary. A suitable orifice structure is also described in U.S. Pat. No. 3,924,180 to Salzman et al. Sheath fluid 16 passes through a conduit 32 having a conductive section 34 which is grounded through a capacitor 35 and a ground wire 36 to minimize noise in the cirucuit.

Sample stream fluid 50 passes through a conduit 40 and into a modulator 42, passing out of the modulator through a conduit 44 having a conductive section 46 which is grounded through a capacitor 47 and ground wire 48 to assist in eliminating noise from an electrical analysis circuit, such as one of those shown in U.S. Pat. No. 3,924,180 to Salzman et al. or U.S. Pat. No. 2,656,508 to Coulter. Such a circuit could be connected to electrodes 24 and 28 to detect the resistance change produced by a particle passing through the region between electrodes 24 and 28.

It is known to those skilled in the art that a problem is encountered in making volumetric measurements on cells utilizing electrical apparatus and that the fluid lines bringing sample and sheath fluids into a flow chamber act as electrical conductors in which electrical noise can be capacitively or magnetically induced. Noise currents in the fluid lines pass through the sensing orifice and are picked up by sensing electrodes such as electrodes 24 and 28 in the instant case. The metal utilized in sections 34 and 46 is preferably a noncorrosive metal such as platinum and is disposed fairly close to the orifice. The metal sections may be grounded by either a simple ground wire or through a capacitor so that any noise within the fluid line is shorted out at that point. Some fluid electrical resistance must remain between the grounded electrodes and the sensing electrodes. In general, the higher this resistance the better. Capacitively shorting out the noise eliminates possible shunting of the DC current through the conductors 24 and 28, which would reduce signal to noise by reducing the output signal at the orifice's sensing electrodes. Noise could be shunted out of the fluid through couplings 34 and 46 even if AC measurements were being taken from at the orifice.

The sample stream fluid 50 may be modulated by modulator 42 which may be, for example, a valve structure for exerting pressure on a soft piece of tubing. Other devices will be apparent to those skilled in the art. The sample stream 50 may come out of the modulator in a diameter varying pattern such as seen in the FIGURE; stream 50 may be modulated in any desired pattern, such as a sinusoidal wave or any kind of a pattern having a predetermined structure which could be programmed into a modulator. The sheath fluid 16 surrounds the sample stream 50. The fluids run in the direction indicated by the arrows 54 out into a vessel for containing them.

A resistance detector 60 is connected to conductors 24 and 28 by wires 62 and 64 and detects changes in resistance across the orifice as the streams 50 and 52 pass therethrough.

It is known that distilled water has very nearly the same dielectric constant as salt solutions in water but has greatly different conductivity. Therefore, the sample stream can comprise distilled water while the sheath fluid comprises a saline solution, or the sample stream can comprise a saline solution while the sheath fluid comprises distilled water. Thus, when the sample stream passes through the orifice 18, the conductivity across the combination of sample and sheath fluids changes in accordance with the diameter of the sample stream fluid as it passes through the orifice. The change in the orifice impedance is almost purely resistive. With the relative resistances of the sample and sheath fluids known, and their comparative volumes known, orifice resistance change is measured as a function of time and compared to the sample fluid pattern established by the modulator to calibrate for cell resistance measurement to be carried out on the apparatus. Cell resistance will vary with cell size and salinity, the latter being preestablished. Thus, cell size can be determined with resistance calibrated.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

What is claimed is:

1. A method of calibrating a cell size measuring apparatus utilizing an electrode surrounded orifice comprising:
   passing a sheath fluid having a first salinity through the orifice;
   passing a sample stream fluid having a second salinity within the sheath fluid through the orifice;
   modulating the diameter of the sample stream in a predetermined pattern; and
   measuring resistive changes across the orifice occurring in accordance with the modulated diameter sample stream.

2. The invention of claim 1 wherein the sheath fluid comprises a fluid of a lower salinity and the sample fluid comprises a fluid of a higher salinity.

3. The invention of claim 2 wherein the fluids comprise water.

4. The invention of claim 1 wherein the sheath fluid comprises a fluid of a higher salinity and the sample stream a fluid of a lower salinity.

5. The invention of claim 4 wherein the fluids comprise water.

6. The invention of claim 1 wherein the sample stream fluid is modulated by pressure variation.

7. The invention of claim 1 further comprising shorting out noise from the sample and sheath fluids prior to their passing through the orifice.

8. An apparatus for calibrating resistance change only in an electrical cell size measuring system comprising:
   means for producing a sample fluid flow and modulating it diameter as a function of time;
   means for enclosing said fluid flow in a sheath fluid flow;
   means for passing said fluid flows through an orifice; and
   means for monitoring resistance change only across said sheath fluid and sample fluid flows as they pass through said orifice in order to provide a measurement of resistance change across said orifice as a function of time.

9. The invention of claim 8 further comprising means for shorting out noise from said sample and sheath fluids prior to their passing through said orifice.

* * * * *